United States Patent [19]
Kelly et al.

[11] 4,053,361
[45] Oct. 11, 1977

[54] PROCESS FOR THE PREPARATION OF GLUCOSE ISOMERASE USING CURTOBACTERIUM

[75] Inventors: Judith Margaret Kelly; John Laurence Meers, both of Stockton-on-Tees, England

[73] Assignee: Imperial Chemical Industries Limited, London, England

[21] Appl. No.: 561,662

[22] Filed: Mar. 24, 1975

[30] Foreign Application Priority Data

Mar. 29, 1974  United Kingdom ............... 13994/74

[51] Int. Cl.$^2$ ...................... C12D 13/10; C07G 7/02; C12D 13/02
[52] U.S. Cl. ............................... 195/66 R; 195/31 F; 195/62; 195/65
[58] Field of Search ..................... 195/31 F, 62, 66 R, 195/65

[56] References Cited
U.S. PATENT DOCUMENTS 3,821,086  6/1974  Lee et al. .......................... 195/65 X
3,956,066  5/1976  Coker et al. ....................... 195/31 F

OTHER PUBLICATIONS

Ichimura et al., "Production and Properties of D-- Glucose Isomerase from *Brevibacterium pentoso-aminoacidium*", Journal of Agricultural Chemical Society of Japan, vol. 39, pp. 291-298 (1965).
Yamada et al., "Taxonomic Studies on Coryneform Bacteria V. Classification of Coryneform Bacteria", J. Gen. Appl. Microbiology, vol. 18, pp. 417-431 (1972).

*Primary Examiner*—Raymond N. Jones
*Assistant Examiner*—Thomas G. Wiseman
*Attorney, Agent, or Firm*—Cushman, Darby & Cushman

[57] ABSTRACT

The production of glucose-isomerizing enzyme by culturing a microorganism of the genus *Curtobacterium* (defined by K Yamada and K Komagata in J Gen Appl Microbiol., 18, 417-31 (1972) at pages 424-5 in a medium containing appropriate nutrients. The *Curtobacterium* strains which may be used include novel strains NCIB 11072 (NRRL B-8069) and NCIB (NRRL B-8068). The enzyme is used in a process for converting glucose to fructose.

7 Claims, No Drawings

PROCESS FOR THE PREPARATION OF GLUCOSE ISOMERASE USING CURTOBACTERIUM

This invention relates to a glucose isomerase enzyme, an enzyme preparation containing glucose isomerase, a method of producing the enzyme or preparation, a method of isomerizing glucose to fructose using the enzyme or preparation and to novel microorganism strains capable of producing the enzyme or preparation.

In recent years a considerable amount of research has been carried out to produce enzymes capable of isomerizing glucose to fructose. Frequently the microorganisms proposed as sources of suitable enzymes have been strains of the *Streptomyces* genus. The enzymes produced by Streptomyces strains very often exhibit considerable activity in isomerizing glucose to fructose but often exhibit a degree of instability which is undesirable for an enzyme which is to be used in a commercial process.

According to the present invention we provide a glucose isomerase enzyme or an enzyme preparation containing glucose isomerase prepared by culturing a microorganism of the *Curtobacterium* genus capable of producing the enzyme or preparation in a medium containing appropriate nutrients.

Further according to the invention we provide a method for producing a glucose isomerase enzyme or an enzyme preparation containing glucose isomerase by culturing a microorganism of the *Curtobacterium* genus capable of producing the enzyme or preparation in a medium containing appropriate nutrients.

Further according to the invention we provide a method for isomerizing glucose to fructose using a glucose isomerase enzyme or an enzyme preparation containing glucose isomerase wherein the enzyme or preparation is produced by culturing a microorganism of the *Curtobacterium* genus, capable of producing the enzyme or preparation, in a medium containing appropriate nutrients.

Further according to the invention we provide *Curtobacterium* species strains NCIB Nos. 11072 and 11073 (NRRL Nos. B-8069 and B-8068 respectively) and variants and mutants thereof capable of producing glucose isomerase.

The genus *Curtobacterium* is a genus comprising strains previously classified as belonging to the genera *Brevibacterium* and *Corynebacterium*.

This genus is defined by K Yamada and K Komagata in J. Gen. Appl. Microbiol., 18, 417–431 (1972) at pp 424–5. The general characteristics of the genus are:

Small short rods. Coccoid cells are found in old cultures. Weakly gram-positive, frequently old cells lose gram-positivity. Generally motile. Motile species show lateral flagellation. Cells multiply by bending type of cell division. Metachromatic granules are not recognised. Pleomorphism is slightly recognised. Ornithine is found in the cell wall as a principal amino acid. Guanine-cytosine content in DNA is distributed from 66 to 71%. Produces acid slowly and weakly from various sugars. Assimilates various kinds of organic acids in addition to acetate, pyruvate and lactate. Gelatin is slowly hydrolysed. Chemoheterotroph. Habitat: Widely distributed in plant materials, soil, etc.

Cultures of the novel Curtobacterium strains GS/4 and LW/3 have been deposited with the National Collection of Industrial Bacteria (NCIB), Torry Research Station, Aberdeen, Scotland, UK and at the US Department of Agriculture, Agricultural Research Service, Northern Regional Research Laboratory (NRRL), Peoria, Illinois and have been given the following NCIB and NRRL Accession Numbers namely:

GS/4 - NCIB 11072 - NRRL B-8069
LW/3 - NCIB 11073 - NRRL B-8068

The mirobiological characteristics of these strains as determined by standard microbiological tests are given in Table 1.

Table 1

| Characteristic | Strain GS/4 | Strain LW/3 |
|---|---|---|
| Colony Description (Oxoid CM3 nutrient agar, 25°, 3 days) | 1mm, circular, entire, convex smooth, slightly yellowish, translucent, soft, easily dispersed, uniform except for several plaques about 4mm diameter on confluent lawn (bacteriophage?) | 0.5mm, circular, entire convex, smooth, yellowish, translucent, slightly coherent, < easily dispersed, uniform. |
| Gram Stain (Oxide CM3 nutrient agar, 25°, 3 days) | Slightly pleomorphic, slenderish, rods, short rods, coccobacilli and cocci, some , singles to small groups, occasional long winding chains of short cells. Usually Gram −, with some Gram +, the latter usually as cocci or coccobacilli. | smallish rods and coccobacilli, some often in groups, Gram + and Gram −, and some cells Gram + with Gram − 'tails'. |
| Motility | + | + |
| Physiology (25°) | | |
| Anaerobic growth | − | − |
| Gelatin hydrolysis, | | |
| - plate (7 days) | + | + |
| - stab (days) | +24 | +7 |
| Casein hydrolysis (milk plate, 7 days) | weak + | + |
| Starch hydrolysis (plate, 7 days) | − or trace | weak + |
| Urease, Christensen's 7 days | − | − |
| Citrate Utilization, Koser's | − | − |
| $NO_3{}' - NO_2{}'$ ($KNO_2$ | | |

Table 1-continued

| Characteristic | Strain GS/4 | Strain LW/3 |
|---|---|---|
| nutrient broth) | + | + |
| Oxidase, Kovacs' | slow + | − |
| Catalase | + | + |
| Acid production in Peptone water sugars: glucose, lactose, sucrose, maltose, fructose, glycrol, starch, mannitol | − | − |
| Egg yolk plate reaction | − | − |
| VP, MR and indole | − | − |
| $NH_3$ from tryptone water | − | − |
| 'Cell wall' analysis | ornithine, galactose, trace of rhamnose, | ornithine, galactose, rhamnose. |
| Source | soil | Woodland litter |

Other strains which may suitably be used in the present invention include glucose isomerase producing strains of *Curtobacterium citreum* - eg NCIB 10702, *Curtobacterium pusillum* - eg NCIB 10354, *Curtobacterium luteum* - eg NCIB 11029, *Curtobacterium helvolum* - eg NCIB 10352 & 10353 and *Curtobacterium alvedum* - eg NCIB 11030. These species were previously classified as belonging to the genus *Brevibacterium*. Their reclassification into the genus *Curtobacterium* is discussed in the article by K Yamada and K Komagata (J. Gen. Appl. Microbiol, 18, 417–431 (1972) at p. 425).

In the method for producing glucose isomerase or an enzyme preparation containing glucose isomerase, the glucose producing microorganism is grown in a culture medium containing a suitable carbon source and other appropriate nutrients and is allowed to form the enzyme. For example an inoculum containing a glucose isomerase producing strain is prepared, eg on an agar slant, and is used to inoculate a suitable culture medium. Here the organism is allowed to grow and to produce glucose isomerase. The incubation period may vary over a wide range depending upon the particular microorganism used and upon the culture medium, preferably it is between 4 and 48 hrs. An aliquot or the entire culture is then used to inoculate a larger volume of nutrient. This may be repeated one or more times.

Microbial cells containing the enzyme may be separated from the final culture medium by any known means. Preferably the whole cells are used to carry out the isomerization of glucose to fructose. However, if desired the enzyme may be extracted from the cells by any suitable method or the final culture medium itself may be used, without separating the cells, in the conversion of glucose to fructose.

The culture medium for the production of the enzyme preparation preferably contains as the carbon source a suitable carbohydrate eg glucose and/or xylose, a suitable organic acid or salt thereof eg an acetate or an alcohol such as ethanol. It may also contain complex organic nutrients such as a vitamin rich broth comprising yeast extract, meat extract etc. The nitrogen source is suitably ammonia, a nitrate, an amino acid or urea and the phosphorus source suitably a phosphate. Other elements present preferably include magnesium, potassium and sulphur, eg added as magnesium sulphate and potassium sulphate and trace elements such as iron, cobalt, zinc, copper, manganese, calcium etc.

The preferred proportions in which the various nutrients are present in the culture medium for production of the enzyme will vary to some extent depending upon the microorganism employed and other factors. Suitable proportions in any particular instance may be determined readily by a competent microbiologist.

During production of glucose isomerase the culture medium is preferably maintained at a temperature within the range 20° to 40° C, especially 28° to 32° C. The optimum temperature for growth of strain NCIB 11073 (NRRL B-8068) is 30° C. Preferably the pH of the medium is maintained within the range 4.5 to 8.0, especially 6.5 to 7.0.

In the isomerization of glucose to fructose by the method of the invention, the time required to reach maximum fructose yields will vary depending upon a number of factors, eg quantity of enzyme or enzyme preparation, manner of preparation of the enzyme (pelleted, extruded etc) source of glucose isomerase or the enzyme preparation, concentration of glucose, temperature, presence or absence of enzyme cofactors etc, usually however suitable yields are obtained in 1 to 36 hrs. During the isomerization the temperature is preferably maintained within the range 20° to 90° C, especially 50° to 75° C. The pH of the glucose-containing medium undergoing isomerization is preferably maintained within the range 5 to 9, particularly 7 to 8.5, if necessary using a suitable buffer system eg a phosphate buffer. However, buffering is to be avoided if posssible in a large scale process. Other activators such as magnesium, cobalt or manganese ions may be present. Enzyme activity may be increased to a maximum by the use of an enzyme cofactor, eg cobalt ions added in the form of a cobalt salt such as cobalt chloride. Very suitably the enzyme or enzyme preparation may be immobilised and used as part of a continuous column process.

The glucose itself may be present in the medium in amounts up to about 70%, preferably 20 to 50%. It may be included in the medium as glucose or as a glucose-syrup containing other sugars, eg maltose, maltotriose and dextrins.

The glucose isomerase or the enzyme preparation containing it is preferably included in the medium in amounts between 4 and 20 GIU (glucose isomerase units) per gram of glucose in the solution. When increasing amounts of enzyme up to several thousand GIU per gram of glucose are added the rate of the isomerization reaction increases.

The glucose isomerase of the present invention may be assayed for its fructose-producing activity by the following assay method:-

GLUCOSE ISOMERASE - ASSAY METHOD

An assay of the activity of the glucose isomerizing enzyme was performed in the following reaction mixture:-

| | |
|---|---|
| 0.2 M phosphate buffer (pH 7.5) | - 0.5 ml |
| 2 M glucose | - 0.5 ml |
| 0.1 M MgSO$_4$.7H$_2$O | - 0.1 ml |
| 0.2 M CoCl$_2$ | - 0.1 ml |
| Enzyme solution | - 0.3 ml |

The solution was made up to 2 ml with distilled water and incubated at 70° C for one hour. The reaction was stopped by adding 4 mls. of 0.5 M perchloric acid and the fructose was determined by the cysteine - carbazole method (Dische Z. & Barenfreund E., J. Beal Chemi, 192, 583 (1951)).

Activity levels of at least 64 units per ml of culture have been observed under standard assay conditions.

The amount of enzyme necessary to produce 1 mg of fructose from glucose per hr at 70° C under the above assay conditions was defined as one unit of enzyme.

The enzyme of the invention is active in isomerizing glucose to fructose and exhibits a satisfactory degree of stability at all temperatures within the range used for the isomerization.

The invention is illustrated by the following Examples:-

EXAMPLE 1

Glucose isomerase was produced by culturing the following microorganisms:-

| | | |
|---|---|---|
| Curtobacterium citreum | | - NCIB 10702 |
| Curtobacterium helvolum | str. 9–8 | - NCIB 10352 |
| Curtobacterium sp. | str. LW/3 | - NCIB 11073 (NRRL B-8068) |
| Curtobacterium sp. | str. GS/4 | - NCIB 11072 (NRRL B-8069) |
| Curtobacterium helvolum | sp. str. 129 | - NCIB 10353 |
| Curtobacterium pusillum | str. 100 | - NCIB 10354 |
| Curtobacterium luteum | str. 2Y12 | - NICB 11029 |

Stock cultures were maintained on nutrient agar slopes at 4° C. Each microorganism was inoculated into a presterilized medium of the following composition:-

| | |
|---|---|
| Meat extract | 5 g/l |
| Yeast extract | 2.5 g/l |
| Peptone | 10 g/l |
| NaCl | 5 g/l |
| MgSO$_4$ | 0.5 g/l |
| CoCl$_2$ | 0.05 g/l |
| D xylose | 10 g/l |

The pH of the medium was adjusted to pH 7.2 prior to inoculation. In each case after incubation at approximately 30° C in air on a rotary shaker for a period of 24 hours, the whole cells were harvested for use as a source of the enzyme.

Using the assay method described above, the activities of the enzymes produced were found to be as follows:-

NCIB 10352 - 64 approx. units/ml after 24 hrs.
NCIB 11073 (NRRL B-8068) - 41 '
NCIB 11072 (NRRL B-8069) - 59 '
NCIB 10353 - 20 '
NCIB 10354 - 12 '
NCIB 10702 - 12 '
NCIB 11029 - 5 '

EXAMPLE 2

Cell material obtained by culturing Curtobacterium helvolum NCIB 10352 as described in Example 1 was inoculated into a 10 liter batch fermenter and was cultivated at 30° C for 24 hrs. Cell material was then centrifugally collected from the fermenter solution, washed with distilled water and freeze-dried.

The freeze-dried material containing the enzyme was added to a medium composed as follows:-

50 gms. glucose
5 mls. 0.1 M MgSO$_4$:7H$_2$O
25 mls. 0.2 M phosphate buffer (pH 7.5)

The total volume was made up to 100 mls with distilled water. The mixture was incubated in a water bath at 65° C for 48 hrs whilst maintaining the pH between 6.8 and 7.2. On completion of the reaction precipitated enzyme was removed by centrifugation at 18000 rpm for 10 mins. The supernatant liquid was treated with an ion exchange resin to remove inorganic salts and protein and was then vacuum evaporated. A transparent sweet syrup containing 58% glucose and 42% fructose was obtained.

We claim:

1. A method for producing a composition selected from the group consisting of glucose isomerase enzyme and enzyme preparations containing glucose isomerase by culturing a microorganism of the Curtobacterium genus capable of producing the composition in a medium containing a carbon source and inorganic nutrients and recovering the composition.

2. A method according to claim 1 wherein the microorganism is selected from the group consisting of strains of Curtobacterium citreum, Curtobacterium pusillum, Curtobacterium luteum, Curtobacterium helvolum and Curtobacterium alvedum.

3. A method according to claim 1 wherein the medium contains as a carbon source a carbohydrate selected from the group consisting of glucose and xylose.

4. A method according to claim 1 wherein the medium contains a nitrogen source selected from the group consisting of ammonia, a nitrate, an amino acid and urea.

5. A method according to claim 1 wherein the medium is maintained at a temperature within the range 20° C to 40° C.

6. A method according to claim 1 wherein the medium is maintained at a pH within the range 4.5 to 8.0.

7. A method for producing a composition selected from the group consisting of glucose isomerase enzyme and enzyme preparations containing glucose isomerase by culturing a micro-organism which is selected from the group consisting of Curtobacterium strain NRRL B-8069, Curtobacterium strain NRRL B-8068 and variants and mutants of said strains in a medium containing a carbon source and inorganic nutrients, and recovering the composition.

* * * * *